United States Patent [19]

Krespan et al.

[11] 4,021,489
[45] May 3, 1977

[54] REACTION OF SULFUR TRIOXIDE WITH CYCLIC (4- AND 5-MEMBERED RING) FLUOROVINYLETHERS

[75] Inventors: Carl George Krespan; Bruce Edmund Smart, both of Wilmington, Del.

[73] Assignee: E. I. Du Pont de Nemours and Company, Wilmington, Del.

[22] Filed: Dec. 8, 1975

[21] Appl. No.: 638,996

[52] U.S. Cl. .................. 260/586 R; 260/327 TH; 260/543 R; 260/543 F

[51] Int. Cl.$^2$ .................................. C07C 45/00

[58] Field of Search ....... 260/586 R, 543 F, 545 R, 260/327 TH

[56] References Cited

UNITED STATES PATENTS

| | | | |
|---|---|---|---|
| 3,244,749 | 4/1966 | Weil | 260/586 R |
| 3,310,584 | 3/1967 | DuBois et al. | 260/586 R |
| 3,330,624 | 7/1967 | Sweeney et al. | 260/586 R |
| 3,333,002 | 7/1967 | Sweeney et al. | 260/586 R |
| 3,338,781 | 8/1967 | Gilbert | 260/586 R |
| 3,341,602 | 9/1967 | Anello et al. | 260/586 R |
| 3,379,765 | 4/1968 | Anello et al. | 260/586 R |
| 3,442,952 | 5/1969 | Sweeney et al. | 260/586 R |
| 3,511,868 | 5/1970 | Gelfand | 260/586 R |

OTHER PUBLICATIONS

Scherer et al., "Ber.", 99, 1966 (1966).
Anello et al., "J. Org. Chem.", 33, 2692 (1968).

*Primary Examiner*—Norman Morgenstern

[57] ABSTRACT

Described is the reaction of $SO_3$ with 4- and 5-membered ring fluorovinyl ethers to produce $\alpha,\beta$-cycloalkenones useful, for example, as mild cationic polymerization initiators.

6 Claims, No Drawings

REACTION OF SULFUR TRIOXIDE WITH CYCLIC (4- AND 5-MEMBERED RING) FLUOROVINYLETHERS

BACKGROUND OF THE INVENTION

1. Field of the Invention

This invention relates to processes for the preparation of $\alpha,\beta$-cycloalkenones and more particularly to the reaction of sulfur trioxide with 4- and 5-membered cyclic fluorovinyl ethers to produce $\alpha,\beta$-cycloalkenones.

2. Prior Art

G. Scherer, G. Horlein, and H. Millauer, Chem. Ber., 99 1966 (1966) describes some reactions of 4- and 5-membered-ring fluorovinyl ethers with $SnCl_4$ or $CaF/FeCl_3$ to produce ketones. A typical reaction is:

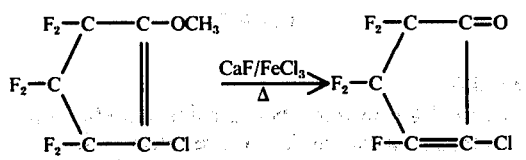

The reactions described are usually performed either at high temperatures or in low yields.

L. G. Anello, A. K. Price, and R. F. Sweeney, J. Org. Chem., 33 2692 (1968); R. F. Sweeney, L. G. Anello, M. M. Schlecter, and B. Veldhuis in U.S. Pat. No. 3,333,002 issued July 25, 1967, disclose syntheses of

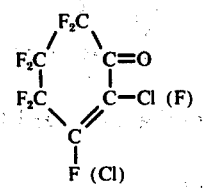

by dehalogenation of perhalocyclohexenes with $SO_3$ in the presence of a catalyst.

SUMMARY OF THE INVENTION

According to the present invention there is provided a process for preparing $\alpha,\beta$-cycloalkenones which comprises contacting and reacting in an inert atmosphere sulfur trioxide and a cyclic fluorovinyl ether of the formula:

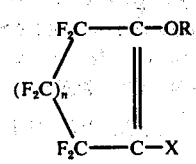

wherein:
X is —H, —Cl, —F, —Br or —OR
R is alkyl of 1–4 carbon atoms, and
n is 0 or 1;
at a temperature in the range of about 0°–50° C and then isolating the products by distilling the reaction mixture at a pot temperature under about 100° C when n is 1 and a pot temperature of about 80°–120° C when n is 0.

DETAILED DESCRIPTION OF THE INVENTION

The present process involves a simple and economical reaction, i.e., inexpensive sulfur trioxide reacting with a cyclic fluorovinyl ether at low temperatures to give a mixture of products which can be isolated by fractional distillation.

The cyclic fluorovinyl ethers used as the starting material are known in the art. Illustrative preparations of these materials are described in the art referred to in the examples. The cyclic fluorovinyl ethers have the structural formula:

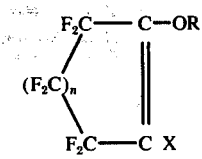

wherein:
X is —H, —Cl, —F, —Br or —OR,
R is alkyl of 1–4 carbon atoms, and
n is 0 or 1.

Preferably, X is —F, —Cl or —OR and R is methyl or ethyl.

The reaction is normally carried out by adding sulfur trioxide to the cyclic fluorovinyl ether at a temperature in the range of about 0°–50° C, preferably at room temperature. An inert atmosphere is provided in order to avoid moisture. No solvent is required, although diluents unreactive toward sulfur trioxide (e.g., fluorocarbons such as Freon 113 of hexafluoropropene (HFP) cyclic dimer) can be employed.

When cyclopentenes are the starting material, the 5-membered ring products are then isolated by direct distillation (preferably in vacuo) at a pot temperature under about 100° C, preferably about 40°–70° C. The anhydride, $FSO_2OSO_2OCH_3$, is the major by-product. If higher distillation pot temperatures are employed, e.g., up to 120° C, a mixture of product, $SO_3$ and methyl fluorosulfate ($CH_3OSO_2F$) is formed which can be very difficult to fractionate.

The 4-membered ring cycloalkenone products prepared from cyclobutenes require higher pot temperatures (about 80°–120° C.) and methyl fluorosulfate ($CH_3OSO_2F$) is the major by-product. Temperatures of 100°–120° C are especially preferred for rapid generation of the 4-membered ring cycloalkenones.

The $\alpha,\beta$-unsaturated ketones can be freed of methyl fluorosulfate by-product where necessary by treatment with dimethyl sulfide, followed by redistillation.

While product can be formed at any molar ratio of sulfur trioxide to cyclic fluorovinyl ether it is preferred that the molar ratio be in the range of about 1:1 to 4:1.

Two moles of sulfur trioxide per mole of fluorovinyl ether are generally required for complete reaction; thus, a particularly preferred ratio is 2:1 to 4:1. With less than 2 moles of sulfur trioxide unreacted fluorovinyl ether is isolated along with the product. In the special case of the reaction of

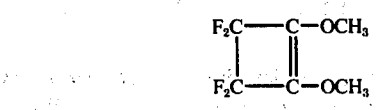

with $SO_3$, 4 moles of sulfur trioxide are recommended.

Typical α,β-cycloalkenones formed from 4-membered, cyclic fluorovinyl ethers are the following:

Perfluorocyclobutenone 3-fluorosulfato-2,4,4-trifluoro-cyclobut-2-en-1-one 2-chloro-3,4,4-trifluoro-cyclobut-2-en-1-one 2-chloro-3-fluorosulfato-4,4-difluorocyclobut-2-en-1-one 3-fluorosulfato-4-fluorocyclobuten-1,2-dione Typical 5-membered ring α,β-cycloalkenones prepared by the present process are:

2-methoxypentafluorocyclopent-2-en-1-one and,

When 4-membered cyclic fluorovinyl ethers of the formula:

$$F_2C\text{---}C\text{---}OR$$
$$F_2C\text{---}C\text{---}X,$$

wehrein X and R are as described previously, are employed, mixtures of the reaction products:

1)
and
2)

are formed; with the exception that when, in the cyclic fluorovinyl ether employed, X=OR, the sole fluorinated α,β-cycloalkenone formed will be:

Methylfluorosulfate ($CH_3OSO_2F$) is formed as a major by-product.

In all cases employing 5-membered cyclic fluorovinyl ethers, the product will be characterized by compounds of the formula:

wherein
  X and R are as described previously, when the preferred process conditions are employed.

The mixed anhydride $FSO_2OSO_2OCH_3$ is formed as a major by-product. When the cyclic fluorovinyl ether, 1,2-dimethoxyhexafluorocyclopentene, of the formula:

is employed, the sulfate compound, is also formed as a major by-product.

EMBODIMENTS OF THE INVENTION

The following examples will serve to illustrate the specific embodiments of the invention. In these examples, temperatures are in degrees centigrade and parts and percentages are by weight.

EXAMPLE 1

Perfluorocyclobutenone and 3-fluorosulfato-2,4,4-trifluorocyclobut-2-en-1-one (I)   $+2SO_3 \rightarrow$   (II)   (III)
$+ CH_3OSO_2F$ A. Using the method of J. T. Burr, et al., J. Amer. Chem. Soc., 72, 4480 (1950), 1-methoxypentafluorocyclobutene of formula (I) was prepared.

B. Reaction of 1 equivalent $SO_3$ with 1 equivalent of (I):

To 21.0g (0.121 mole) of (I) in a flask at room temperature equipped with a water condenser and its outlet to a −78° trap was added 5.0 g. (0.12 mole) of sulfur trioxide over ca. a 30-min period (exotherm to 45°). All operations were performed in a nitrogen atmosphere. No volatiles collected in the trap. The reaction mixture was then distilled in vacuo with an intervening −78° trap to give 5.2g of mostly (I) bp 40°–47° (195 mm), 13 g of ca. 74% (I) and 26% $CH_3OSO_2F$, bp 47°–48° (195 mm), and 2.6 g of (III) bp 41°–43° (30 mm). The trap contained about 1 ml of (II), identified by infrared (IR) (gas) 1845, 1725 $cm^{-1}$.

C. Reaction of 2 equivalents $So_3$ with 1 equivalent of (I):

In a substantial repetition of B, to 17.4 g (0.1 mole) of (I) was added dropwise 8.4 ml (16 g. 0.2 mole) of $SO_3$ over a 30-min period (exotherm to about 45°). After the reaction mixture cooled to room temperature, a fractionating column was attached and the mixture was slowly heated. No distillation occurred until the pot temperature reached 90°–100° and 3.1 g of pure (II) was collected (pot temperature to 110°): bp 45°–46°. Structure (II) was confirmed by the following: IR (gas) 1845, 1727 $cm^{-1}$; nmr ($CCl_4$) $\phi$ −101.3 (complex m, 1), −112.9 (complex m, 1), −116.2 (complex m, 3); mass spec (rel int) m/e: 93 (111, P-CO,F), 112 (771, P-CO), 140 (285, P) 124 (78), 121 (67), 74 (60), 71 (57), 69 (36).

The distillation was continued on the residue to give 11.1 g of mostly $CH_3OSO_2F$: bp 75°–88°, 52°–48° (180–160 mm), and 8.4 g of (III): bp 58°–62° (60 mm) (mostly 62°). Structure (III) was confirmed by the following: IR (neat) 1838 $cm^{-1}$, 1702 $cm^{-1}$, nmr ($CCl_4$) $\phi$ + 45.1 (d of t, 1, J = 3.8, 1.7 Hz), −104.2 (t of d, 1, J = 17.8, 3.8 Hz), −112.9 (d of d, 2, J = 17.8, 1.7 Hz).

Anal. Calcd for $C_4F_4O$ (II): C, 33.78; Found: C 34.31
Calcd for $C_4F_4O_4S$ (III): C, 21.83; F, 34.53; Found: C, 21.90; F, 34.46.

Utility Example A

Practical grade butyl vinyl ether, 12.7 ml, 10 g, was chilled to ca. −10° and treated with 2 drops of perfluorocyclobutenone of formula (II) prepared in Example 1. After stirring 5 min, the solution was slowly warmed to room temperature where it was allowed to stand 24 hr. The resultant viscous mixture was concentrated in vacuo to give 8.0 g of thick oil; M.W. (ebull. in benzene) 1095, indicating an average of 11 vinyl units per chain. The oil is useful as a film former.

EXAMPLE 2

2-chloro-3,4,4-trifluorocyclobut-en-1-one and 2-chloro-3-fluorosulfato-4,4-difluorocyclobut-en-1-one

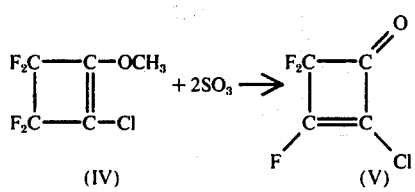

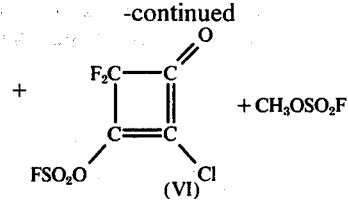

A. Using the preparation described by J. P. Park, C. M. Snow, and R. J. Lacher, J. Amer. Chem. Soc., 73,2343 (1951), 1-methoxy-2-chloro-tetrafluorocyclobutene of formula (IV) was prepared.

B. Sulfur trioxide, 8.4 ml (0.2 mole), was added dropwise at room temperature to 19.0 g (0.10 mole) of (IV) over a 30-min period (exotherm to 58°). The dark reaction mixture was distilled (pot temp 110°) to give 2.7 g of a mixture of 30% (V) and mostly $CH_3OSO_2F$: bp 63°–65°; 4.7 g of ca. 20% (V) 80% $CH_3OSO_2F$: bp 80°–82°; 8.0 g of $CH_3OSO_2F$: bp 85°–87°, 48°–52°(180 mm), and 10.7 g of (VI): bp 75°–80° (mostly 78°–80°) (60 mm). The structure for (VI) was confirmed by the following: IR (neat) 1823 $cm^{-1}$, 1630 $cm^{-1}$; nmr ($CCl_4$) $\phi$ +45.6 (t, 1, J = 5 Hz, −109.5 (d, 2, J = 5 Hz).

Anal. Calcd for $C_4ClF_3O_4S$ (VI): C, 20.31; F, 24.09; Found: C, 20.67: F, 24.15.

The presence of (V) in the mixture was confirmed by IR and nmr: IR (neat) 1822 $cm^{-1}$, 1668 $cm^{-1}$; nmr ($CCl_4$) $\phi$ −88.6 (t, 1, J 5.2 Hz), −113.9 (d, 2, J = 5.2 Hz).

Utility Example B

Practical grade butyl vinyl ether, 12.7 ml, 10 g, was treated with 2 drops of 2-chloro-3-fluorosulfato-4-difluorocyclobut-2-en-1-one of formula (VI) at −10°, and 9.8 of viscous oil was recovered after 24 hr at room temperature; M. W. 970 (ebull. in benzene), indicating an average of 10 vinyl units per chain. The oil is useful as a film former.

EXAMPLE 3

3-Fluorosulfato-4-fluorocyclobuten-1,2-dione

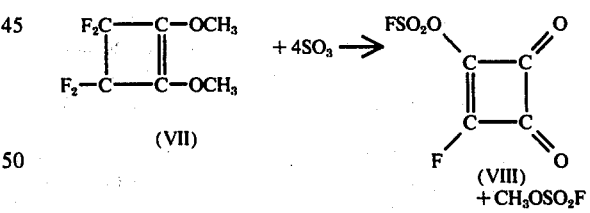

A. Using the method of J. C. Park, S. D. Sharrah, and J. R. Lacher, J. Amer. Soc., 71, 2337 (1949), 1,2-dimethoxy-tetrafluorocyclobutene of formula (VII) was prepared.

B. Sulfur trioxide, 16.8 ml (0.4 mole) was added dropwise to 18.6 g (0.1 mole) of (VII) while keeping the reaction temperature below 50°. After stirring overnight, the colorless reaction mixture was distilled as a pot temperature of 80°–90° to give 25.4 g of mostly $CH_3OSO_2F$: bp 46°–52° (180–160 mm). The pot residue became progressively more viscous and darkened as the distillation proceeded. Continued fractionation gave 5.8 g of mostly (VIII), 3-fluorosulfato-4-fluorocyclobuten-1,2-dione: bp 57°–58° (2 mm). Structure (VIII) was confirmed by: IR (neat) 1810 $cm^{-1}$, 1665 cm$^{-1}$ (broad); nmr (neat, ext. ref.) $\phi + 46.3$ (d, 1, J = 2.6 Hz), −72.9 (d, 1, J = 2.6 Hz). Product (VIII) rapidly hydrolyzes to squaric acid

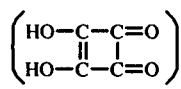

on atmospheric exposure.

EXAMPLE 4

2-Chloropentafluorocyclopent-2-en-1-one

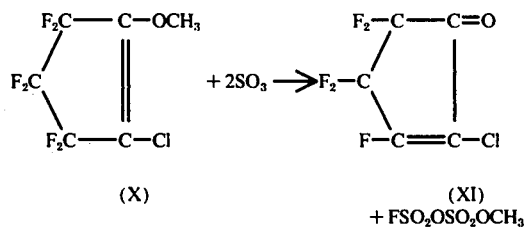

A. 1-Chloro-2-methoxyhexafluorocyclopentene of formula (X) was prepared as described by L. G. Anello, A. K. Price, and R. F. Sweeney, J. Org. Chem., 33, 2696 (1968).

B. Reaction of 1 equivalent $SO_3$ with 1 equivalent of (X):

To 48.1 g (0.20 mol) of 1-chloro-2-methoxyhexafluorocyclopentene stirred at 0°–5° was added dropwise 17.6 g (0.22 mol) of $SO_3$. After addition had been completed, the cooling bath was removed and the mixture stirred while a slight exotherm carried the temperature to 30°. The mixture was allowed to stand over the weekend, then distilled under vacuum with the heating bath at ca 70° to give 17.4 g (82% yield) of mixed anhydride, bp 41° (4.5 mm). The by-product is confirmed by: IR (CaF$_2$ plates) 3.35 (satd CH), 6.75 and 6.95$\mu$(SO$_2$O): nmr $^1$H 4.31 ppm (s, OCH$_3$): $^{19}$F 45.0 ppm (s, SO$_2$F).

Anal. Calcd for CH$_3$FO$_6$S$_2$: C, 6.19; H, 1.56: F, 9.79; S, 33.03; Found: C, 6.35; H, 1.63; F, 10.22; S, 32.63.

IR analysis of the contents of the cold trap indicated a mixture of unsaturated ketone (XI), 2-chloropentafluorocyclopent-2-en-1-one, and the starting vinyl ether (X).

C. Since 2:1 stoichiometry seemed necessary for a more complete reaction, a similar reaction of 48.1 g (0.20 mol) of the vinyl ether (X) and 35.2 g (0.44 mol) of SO$_3$ was carried out. In this case distillation during which the bath temperature was up to 120° resulted in a mixture of (XI) and methyl fluorosulfate, bp 50°–59°(220 mm) which could not be fractionated apart. Attempts to remove methyl fluorosulfate by refluxing the mixture with anhydrous NaF or heating with epichlorohydrin failed, but treatment with dimethyl sulfide gave a solid mass from which (XI) was distilled (11.6 g). Redistillation gave pure (XI) bp 93°. Structure (XI) was confirmed by: IR 5.60 (C=O), 6.00 (C=C), 7.3–9 (CF), 13.22$\mu$ (C-Cl): nmr $^{19}$F−110 (t,J$_{FF}$19.2Hz, into t, J$_{FF}$4.5Hz, 1, =CF),−123 (d,J$_{FF}$19.2Hz, into rough t, J$_{FF}$∼1Hz,2, =CCF$_2$), −126 ppm (d,J$_{FF}$4.5H$_z$, into rough $t$, J$_{FF}$∼1Hz, 2, CF$_2$).

Anal. Calcd for C$_5$ClF$_5$O (XI): C, 29.08; Cl, 17.17; F, 46.00; Found: C, 28.79; Cl, 17.04; F, 46.22.

Finally, 36.7 g (0.157 mol) of 1-chloro-2-methoxyhexafluorocyclopentene (X) and 25.6 g (0.32 mol) of $SO_3$ were reacted at 0° stirred over the weekend at 25°, and fractionated at low head temperature and a pot temperature of 70°. Crude (XI), bp 37°–41° (100 mm) and trap liquid were treated with anhydrous NaF and redistilled to give 24.8 g (77% yield based on (X)) of pure (XI), bp 58° (200 mm). Also isolated in the preliminary fractionation was 25.3 g (83% yield based on $SO_3$) of anhydride by-product bp 43°–44° (4.5 mm).

EXAMPLE 5

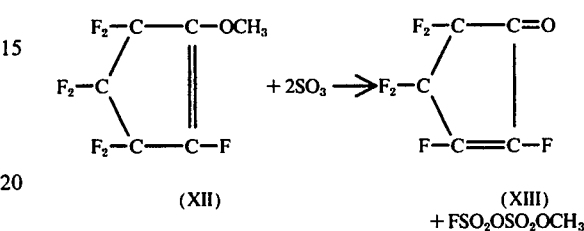

Using the method of R. F. Stockel, M. T. Beacham and F. H. Megson, Can. J. Chem., 42, 2880 (1964), 1-methoxyheptafluorocyclopentene of formula (XII) was prepared in 78% yield.

Addition of 16.0 g (0.20 mol) SO$_3$ to 22.4 g (0.10 mol) of 1-methoxyheptafluorocyclopentene (XII) at 5°, stirring at 25° for 2 days, and distillation at low temperature gave crude (XIII), bp 31°–32° (200 mm), and 14.0 g (72% yield based on SO$_3$) of anhydride bp 43°–44° (4 mm). Treatment of the crude (XIII) and trap liquid with anhydrous NaF followed by distillation at a pot temperature of 70° afforded 16.0 g (84% yield based on XII) of pure (XIII), bp 66°. Structure (XIII) was confirmed by: IR(CCl$_4$) 5.58 (C=O), 5.80 (C=C), 7.1–8.7$\mu$(CF); nmr $^{19}$F −122.3 (d,J$_{FF}$13.1Hz, into d,J$_{FF}$9.4 Hz, 2, C=CCF$_2$), −127.1 (d, J$_{FF}$4.3 Hz, into overlapping t, J$_{FF}$4.3 Hz, 2, CF$_2$), −129.2 (t, J$_{FF}$13.1 Hz, into t, J$_{FF}$4.0Hz, 1, FC=CFC=O), −143.8 ppm (t, J$_{FF}$9.4 Hz, into overlapping t, J$_{FF}$4.7Hz, 1, FC=CFC±O).

Anal. Calcd for C$_5$F$_6$O (XIII): C, 31.60; F, 59.98; Found: C, 31.23; F, 60.42.

EXAMPLE 6

2-Methoxypentafluorocyclopent-2-enone

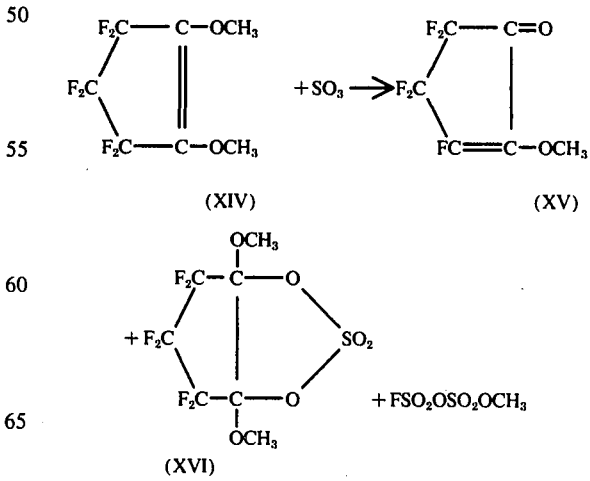

A. 1,2-Dimethoxyhexafluorocyclopentene of formula (XIV) was prepared in 63% yield by an adaptation of the method of R. F. Stockel, M. T. Beacham, and F. H. Megson, Can. J. Chem., 42, 2880 (1964).

B. Dropwise addition of 16.0 g (0.20 mol) of $SO_3$ to 23.6 g (0.10 mol) of 1,2-dimethoxyhexafluorocyclopentene (XIV) at 0° was followed by warming to 25°. A mild exotherm was controlled at 30° or less, then the mixture was allowed to stand at 25° overnight. Distillation at low temperature (pot at 55°–65°) gave 12.4 g (16% yield based on XIV) of enone (XV), bp 38°–39° (6mm), 10.9 g (56% yield based on $SO_3$) of crude anhydride, bp ~48° (5mm), identified by nmr, and 3.2 g (10% yield based on XIV) of sulfate (XVI). Redistillation of (XV) gave an analytical sample, bp 62° (30 mm). Structure (XV) was confirmed by: IR(neat) 3.29, 3.36, and 3.48 (satd CH), 5.61 (C=O), 5.93 (C=CF), 7–10μ(CF,COC); nmr $^1H$ 4.20 ppm (d, $J_{HF}$3.1Hz, OCH$_3$); $^{19}F$ –120.4 (d, $J_{FF}$13.7Hz, into m, 2, C=CCF$_2$), –126.7 (d, $J_{FF}$5.3Hz, into t, $J_{FF}$1.3Hz, 2, CF$_2$), –140.0 ppm (t,$J_{FF}$13.7Hz, into t,$J_{FF}$5.3Hz into overlapping q, $J_{HF}$3Hz).

Anal. Calcd for $C_6H_3F_5O_2$ (XV): C, 35.66; H, 1.49; F, 47.01. Found: C, 35.62; H, 1.54; F, 47.40.

Utility Example C

A solution of dimethyl sulfide in hexane was used as prototype of a petroleum fraction containing sulfur impurities. An α,β-unsaturated fluorocycloketone was shown to precipitate solid adduct from solution and, as shown in Example 4, above, the adduct can be pyrolyzed to regenerate unsaturated ketone. Thus, the products of this invention are useful in assaying sulfur-containing impurities in petroleum. They may also be used to remove sulfides as adducts from which the unsaturated fluoroketone is recoverable by thermolysis.

To a solution of 0.62 g (0.010 mol) of dimethyl sulfide in 12.4 g of n-hexane (ca.5% sulfide by weight was added 2.27 g (0.011 mol) of the 2-chloropentafluorocyclopent-2-enone of Example 4. Immediate cloudiness and formation of precipitate was observed. After having stood at 25° over the weekend, the supernatant liquid was shown by $^1H$ nmr analysis to have been reduced in sulfide concentration by 30%. After 11 days, the reduction was 66%.

Utility Example D

The unsaturated fluorocycloketones are mild cationic polymerization initiators.

A mixture of 15.00 g (0.15 mol) of practical grade vinyl butyl ether and 0.6 g of the 2-chloropentafluorocyclopent-2-enone of Example 4 was stirred at 0° for 30 min., then allowed to warm to 25° with stirring. After standing overnight, the viscous mixture was evacuated at full pump and 25° to give a residual thick oil, wt. 15.1 g. M.W. (ebull. in benzene) was 688, indicating an average of 7 vinyl ether units per chain.

What is claimed is:

1. A process for preparing α,β-cycloalkenones which comprises contacting and reacting in an inert atmosphere sulfur trioxide and a cyclic fluorovinyl ether of the formula:

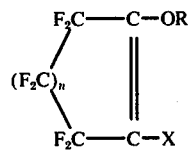

wherein:
X is —H, —Cl, —F, —Br or —OR,
R is alkyl of 1–4 carbon atoms, and
n is 0 or 1;
at a temperature in the range of about 0°–50° C and then isolating the products by distilling the reaction mixture at a pot temperature under about 100° C when n is 1 and a pot temperature of about 80°–120° C when n is 0.

2. The process of claim 1 wherein the molar ratio of sulfur trioxide to fluorovinyl ether is in the range of about 1:1 to 4:1.

3. The process of claim 2 wherein R is methyl or ethyl and X is —F, —Cl or —OR.

4. The process of claim 1 wherein the molar ratio or sulfur trioxide to fluorovinyl ether is in the range of about 2:1 to 4:1.

5. The process of claim 4 wherein the distillation is conducted under a vacuum when n is 1 at a pot temperature of about 40°–70° C and is conducted at a pot temperature of about 100°–120° C when n is 0.

6. The process of claim 5 wherein the cyclic fluorovinyl ether is selected from the group consisting of 1-methoxy-pentafluorocyclobutene, 1-methoxy-2-chlorotetrafluorocyclobutene, 1,2-dimethoxy-tetrafluorocyclobutene, 1-chloro-2-methoxyhexafluorcyclopentene, 1-methoxyheptafluorocyclopentene and 1,2-dimethoxyhexafluorocyclopentene.

* * * * *